(12) United States Patent
Hetherington et al.

(10) Patent No.: US 9,258,999 B2
(45) Date of Patent: *Feb. 16, 2016

(54) BIOPESTICIDE COMPOSITIONS COMPRISING WATER SOLUBLE POLYOLS

(71) Applicant: MPT Mustard Products & Technologies Inc., Saskatoon (CA)

(72) Inventors: Mark Andrew Hetherington, Saskatoon (CA); James Robinson, Hague (CA)

(73) Assignee: MPT Mustard Products & Technologies, Inc., Saskatoon (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/449,665

(22) Filed: Aug. 1, 2014

(65) Prior Publication Data

US 2015/0037310 A1 Feb. 5, 2015

Related U.S. Application Data

(60) Provisional application No. 61/861,518, filed on Aug. 2, 2013.

(51) Int. Cl.
*A01N 43/16* (2006.01)
*A01N 25/02* (2006.01)
*A01N 43/38* (2006.01)
*A01N 51/00* (2006.01)

(52) U.S. Cl.
CPC .............. *A01N 43/16* (2013.01); *A01N 25/02* (2013.01); *A01N 43/38* (2013.01); *A01N 51/00* (2013.01)

(58) Field of Classification Search
None
See application file for complete search history.

(56) References Cited

U.S. PATENT DOCUMENTS

| | | | | |
|---|---|---|---|---|
| 5,770,789 A | * | 6/1998 | Mitchell-Olds et al. | 800/265 |
| 7,901,701 B2 | * | 3/2011 | Winowiski et al. | 424/405 |
| 8,450,244 B2 | * | 5/2013 | Robinson | 504/118 |
| 2003/0194455 A1 | * | 10/2003 | Taylor | 424/755 |
| 2004/0133936 A1 | * | 7/2004 | Rossiter et al. | 800/278 |
| 2013/0164365 A1 | * | 6/2013 | Talalay et al. | 424/450 |

FOREIGN PATENT DOCUMENTS

WO 2010023162 3/2010

OTHER PUBLICATIONS

Brown, J. and Morra, M.J., "Glucosinolate-Containing Seed Meal as a Soil Amendment to Control Plant Pests 2000-2002", Subcontract Report National Renewable Energy Laboratory NREL/SR-510-35254, Jul. 2005.
Morra, M.J, "Chemical Characterization and Release Efficiency of Defatted Mustard Meals 2000-2002", Subcontract Report National Renewable Energy Laboratory NREL/SR-510-36208, Jul. 2005.
Rodman, J.E., "A Taxonomic Analysis of Glucosinolate-Producing Plants, Part 1: Phenetics", Systematic Botany, (1991), 16:598-618.
Toribio et al., "Strong ion-exchange centrifugal partition chromatography as an efficient method for the large-scale purification of glucosinolates", J. of Chromatography, v. 1170, p. 44-51 (2007).
West et al., "Single column approach for the liquid chromatographic separation of polar and non-polar glucosinolates from broccoli sprouts and seeds", J. of Chromatography v. 996, p. 227-232 (2002).

* cited by examiner

*Primary Examiner* — Ralph Gitomer
(74) *Attorney, Agent, or Firm* — Bereskin & Parr LLP/S.E.N.C.R.L., s.r.l.; Micheline Gravelle

(57) ABSTRACT

Provided are liquid compositions comprising inactive biopesticide precursors comprising a glucosinolate concentrate, a plant material comprising a myrosinase enzyme complex, and a water soluble polyol. Further provided are methods of making and using such compositions.

11 Claims, No Drawings

BIOPESTICIDE COMPOSITIONS COMPRISING WATER SOLUBLE POLYOLS

RELATED APPLICATION

This application claims benefit of 35. U.S.C. 119 based on the priority of corresponding Provisional Patent Application No. 61/861,518, filed on Aug. 2, 2013, which is incorporated herein in its entirety.

FIELD OF THE DISCLOSURE

The present disclosure relates to novel liquid compositions comprising compounds obtainable from plants for the treatment of pests and methods of making and using such compositions.

BACKGROUND OF THE DISCLOSURE

The following paragraphs are not an admission that anything discussed in them is prior art or part of the knowledge of persons skilled in the art.

Various pesticide compositions obtainable from natural sources are known to the prior art. These so-called "biopesticides" may be prepared from, for example, plants. Thus products prepared from mustard plants have been demonstrated to exhibit inhibitory effects against arthropods, weeds, fungi and bacteria. (see: Brown, J. and Morra M. J., 2005, Subcontract Report National Renewable Energy Laboratory NREL/SR-510-35254). Further biopesticide compositions obtainable from plants are provided by Applicant's co-pending application, U.S. patent application Ser. No. 14/314,661, which is incorporated by reference herein, and which discloses inactive biopesticide precursors. The inactive biopesticide precursors do not have pesticidal properties themselves, thus facilitating safe storage and transportation. The disclosed compositions are provided in dry form, or as a two component system. Other inactive dry inactive compositions are also known to the art (see e.g.: U.S. Pat. No. 7,901,701). Mixing with water of the dry biopesticide precursor compounds is required to obtain active biopesticide. In some operational settings, notably where the use of substantial volumes of biopesticide is involved, for example in large scale agricultural operations, mixing of dry biopesticide precursor compounds with water may be less desirable. Large mixing tanks are required, and upon mixing the active biopesticide needs to be transferred to devices used for pesticide application, such as a sprayer or an irrigation system. In particular, where an irrigation system is used for application of the biopesticide, it is desirable that the biopesticide precursor compounds are available in liquid form and can directly enter the irrigation system. Furthermore, where the biopesticide precursor compounds are provided in dry form or other form which is not readily miscible with water (e.g. when formulated with oil as a carrier), deviations from the optimal mixing conditions may lead to partial solution of the dry compounds in water, and consequentially loss of pesticide potency. Finally, the preparation of dry biopesticide compounds requires the removal of water from plant material, which represents a cost factor.

There are therefore still significant shortcomings in plant material based compositions capable of controlling pests known to the prior art. In particular, there is a need for liquid compositions that comprise inactive biopesticide precursor compounds.

SUMMARY OF THE DISCLOSURE

The following paragraphs are intended to introduce the reader to the more detailed description that follows and not to define or limit the claimed subject matter.

The present disclosure relates to liquid compositions for the treatment of pests. Accordingly, the present disclosure provides, in at least one aspect, at least one embodiment comprising a liquid composition comprising an inactive biopesticide precursor substantially free of glucosinolate breakdown products, said liquid composition comprising:
(a) a glucosinolate concentrate;
(b) an active myrosinase complex in a concentration sufficient to release an effective amount of glucosinolate breakdown products upon the addition of water; and
(c) a water soluble polyol.

In a further embodiment, in accordance with the present disclosure, the active myrosinase is obtained or obtainable from a plant material. The plant material is preferably obtained from or obtainable from mustard plants.

In a further preferred embodiment, the water soluble polyol is glycerol, polyethylene glycol or propylene glycol.

The present disclosure, in a further embodiment, provides a method for making a liquid composition comprising an inactive biopesticide precursor comprising mixing:
(a) a glucosinolate concentrate;
(b) an active myrosinase complex in a concentration sufficient to release an effective amount of glucosinolate breakdown products upon the addition of water; and
(c) a water soluble polyol
to obtain a mixture substantially free of glucosinolate breakdown products.

The present disclosure, in a further embodiment, provides a method for controlling pests comprising:
(a) providing a liquid composition comprising an inactive biopesticide precursor substantially free of glucosinolate breakdown product, said liquid composition comprising:
(i) a glucosinolate concentrate;
(ii) an active myrosinase complex in a concentration sufficient to release an effective amount of glucosinolate breakdown products upon the addition of water to the liquid composition; and
(iii) a water soluble polyol;
(b) adding water to the liquid composition to obtain a diluted liquid composition; and
(c) applying the diluted liquid composition to a pest.

In further embodiments, the present disclosure provides a pesticide application kit containing a liquid formulation comprising:
(a) a glucosinolate concentrate;
(b) an active myrosinase complex in a concentration sufficient to release an effective amount of glucosinolate breakdown products upon the addition of water; and
(c) a water soluble polyol,
together with instructions regarding the addition of water to the liquid formulation to form a diluted liquid formulation and subsequent application to a pest.

Other features and advantages of the present disclosure will become apparent from the following detailed description. It should be understood, however, that the detailed description, while indicating preferred embodiments of the disclosure, are given by way of illustration only, since various changes and modifications within the spirit and scope of the disclosure will become apparent to those of skill in the art from the detailed description.

DETAILED DESCRIPTION OF THE DISCLOSURE

Various compositions or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions or processes having all of the features of any one composition, system or process described below or to features common to multiple or all of the compositions, systems or processes described below. It is possible that a composition, system or process described below is not an embodiment of any claimed subject matter. Any subject matter disclosed in a composition, system or process described below that is not claimed in this document may be the subject matter of another protective instrument, for example, a continuing patent application, and the applicants, inventors or owners do not intend to abandon, disclaim or dedicate to the public any such subject matter by its disclosure in this document.

It should be noted that terms of degree such as "substantially", "about" and "approximately" as used herein mean a reasonable amount of deviation of the modified term such that the end result is not significantly changed. These terms of degree should be construed as including a deviation of the modified term if this deviation would not negate the meaning of the term it modifies.

As used herein, the wording "and/or" is intended to represent an inclusive-or. That is, "X and/or Y" is intended to mean X or Y or both, for example. As a further example, "X, V, and/or Z" is intended to mean X or Y or Z or any combination thereof.

All publications, patents and patent applications are herein incorporated by reference in their entirety to the same extent as if each individual publication, patent or patent application was specifically and individually indicated to be incorporated by reference in its entirety.

As hereinbefore mentioned, the present disclosure relates to liquid compositions for the treatment of pests. The compositions of the present disclosure are particularly useful in that they comprise inactive biopesticide precursor compounds, facilitating storage and transportation thereof. Furthermore the compositions of the present disclosure are liquid and are readily miscible with water to obtain an active biopesticide. In accordance with the current disclosure it has been found that the liquid compositions of the present disclosure comprise inactive precursors that are not converted to an active biopesticide, unless the compositions are mixed with sufficient quantities of water. Furthermore, the liquid compositions of the present disclosure comprise substantial quantities of biopesticide precursors dissolved in a water soluble polyol. Surprisingly, formulation of the biopesticide precursors in the presence of the water soluble polyol does not negatively impact the potency of the biopesticide and upon mixing with sufficient quantities of water an active pesticidal compound is obtained. The formulations, upon mixing with sufficient quantities of water, are substantially pesticidally active. The formulations of the present disclosure provide the biopesticide precursors in a single liquid formulation. The foregoing features of the compositions of the present disclosure render these compositions particularly attractive for use in conjunction with application to pests using agricultural irrigation systems.

In accordance herewith, in one aspect the present disclosure provides a liquid composition comprising an inactive biopesticide precursor substantially free of glucosinolate breakdown products, said liquid composition comprising:

(a) a glucosinolate concentrate;

(b) an active myrosinase complex in a concentration sufficient to release an effective amount of glucosinolate breakdown products upon the addition of water; and (c) a water soluble polyol The term "glucosinolate" as used herein refers to a class of chemical compounds having a structural formula (I):

(I)

wherein R is a derivative of an amino acid, including methionine, phenylalanine, tyrosine or tryptophan, including any of the derivatives of any of the foregoing amino acids having the exemplary R-groups included in chemical compounds (II); (III); (IV); or (V), as shown below, and, further, including the exemplary R-groups shown in Table VII below. Examples of glucosinolates include, but are not limited to, progoitrin, epiprogoitrin, sinigrin and sinalbin. "Progoitrin" as used herein refers to a chemical compound having an (R)-2-hydroxy-3-butenyl R-group and having a structural formula (II):

(II)

"Epiprogoitrin" as used herein refers to a chemical compound having an (S)-2-hydroxy-3-butenyl R-group and a structural formula (III):

(III)

"Sinigrin" as used herein refers to a chemical compound having an allyl R-group and a structural formula (IV):

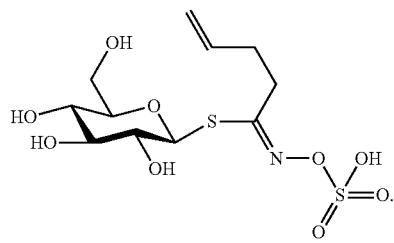

(IV)

"Sinalbin" as used herein refers to chemical compounds having a p-hydroxybenzyl R-group and a structural formula (V):

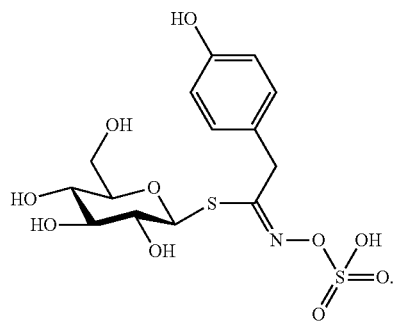

(V)

The term glucosinolate further refers to chemical compounds that are precursor compounds to certain substantially active pesticidal compounds, but are themselves substantially inactive as pesticides. Additional exemplary R-groups of glucosinolates are set forth in Table VII below.

The term "glucosinolate breakdown product", as used herein refers to chemical compounds obtainable from the hydrolysis of glucosinolate. These compounds include, but are not limited to, three classes of glucosinolate breakdown products known as nitrile, thiocyanate and isothiocyanate. Thus glucosinolate products may include a nitrile, a thiocyanate or an isothiocyanate, and/or mixtures of any two, or three of the aforementioned classes of compounds. As used herein "nitrile" refers to a class of chemical compounds having a structural formula (VI):

 (VI), wherein R is a derivative of an amino acid, including methionine, phenylalanine, tyrosine or tryptophan, including any of the specific derivatives of the foregoing amino acids having the R-groups shown included in chemical compounds (II); (III); (IV); or (V) (with reference to chemical compound (I); i.e. a (R)-2-hydroxy-3-butenyl; (S)-2-hydroxy-3-butenyl; allyl; and p-hydroxybenzyl R-group, respectively) and, further, including any of the R-groups shown in Table VII below. As used herein "thiocyanate" refers to a class of chemical compounds having a structural formula (VII):

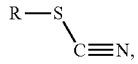 (VII)

wherein R is a derivative of an amino acid including methionine, phenylalanine, tyrosine or tryptophan, including any of the specific derivatives of the foregoing amino acids having the R groups shown included in chemical compounds (II); (III); (IV); or (V) (with reference to chemical compound (I); i.e. a (R)-2-hydroxy-3-butenyl; (S)-2-hydroxy-3-butenyl; allyl; and p-hydroxybenzyl R-group, respectively) and, further, including any of the R-groups shown in Table VII below. As used herein "isothiocyanate" refers to a class of chemical compounds have a structural formula (VIII):

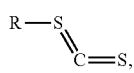 (VIII)

wherein R is a derivative of an amino acid including methionine, phenylalanine, tyrosine or tryptophan, including any of the specific derivatives of the foregoing amino acids having the R groups shown included in chemical compounds (II); (III); (IV); or (V) (with reference to chemical compound (I); i.e. a (R)-2-hydroxy-3-butenyl; (S)-2-hydroxy-3-butenyl; allyl; and p-hydroxybenzyl R-group, respectively) and, further, including any of the R-groups shown in Table VII below.

Further examples, without limitation, of nitrile compounds in accordance herewith are 1-cyano-2-hydroxy-3-butene and alyl cyanide. As used herein is "1-cyano-2-hydroxy-3 butene" refers to a chemical compound having a structural formula (IX):

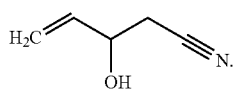

(IX)

As used herein "alyl cyanide" refers to a chemical compound having a structural formula (X):

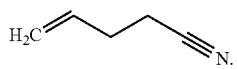

(X)

In accordance herewith, the nitrile may be 1-cyano-2-hydroxy-3 butene or alyl cyanide or a mixture thereof.

A further example, without limitation, of a thiocyanate in accordance herewith is allyl thiocyanate. "Allyl thiocyanate" or "ATC" as used interchangeably herein refers to a chemical compound having the structural formula (XI):

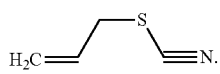

(XI)

A further example, without limitation, of an isothiocyanate compound in accordance herewith is allyl isothiocyanate (AITC). "Allyl isothiocyanate" or "AITC" as used interchangeably herein refers to a chemical compound having the structural formula (XII):

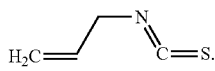

(XII)

Still further exemplary glucosinolate breakdown products, without limitation, in accordance herewith are goitrin and epithionitrile. "Goitrin" or "oxazolidine-thione" as may interchangeably be used herein refers to a chemical compound having the structural formula (XIII):

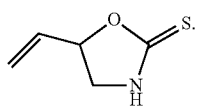

(XIII)

"Epithionitrile" as used herein refers to a chemical compound having the structural formula (XIV):

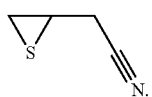

(XIV)

The hereinbefore glucosinolate breakdown products are substantially active as pesticides.

The terms "myrosinase", "myrosinase complex" and "active myrosinase complex" which all may be used herein, refer to any enzyme, enzyme complex or enzyme assembly capable of converting glucosinolates, including but not limited to progoitrin, epiprogoitrin, sinigrin and sinalbin, into substantially pesticidally active glucosinolate breakdown products, including, but not limited to, any pesticidally active nitrile, including, but not limited to, 1-cyano-2-hydroxy-3 butene, and allyl cyanide; any pestidally active thiocyanate, including but not limited to, ATC; any pesticidally active isothiocyanate, including, but not limited to, AITC; goitrin and epithionitrile; and any nitrile, thiocyanate and isothiocyanate having an R-group set forth in Table VII. The activity of myrosinase is expressed herein in units per gram, wherein 1 unit of myrosinase activity is defined as the amount of enzyme required to hydrolyze 1 micromole of glucosinolate per minute at pH 6.5 and at a temperature of 22° C.

Glucosinolate Concentrate

In accordance with certain aspects hereof, the liquid compositions provided in the present disclosure comprise a glucosinolate concentrate. In certain embodiments the glucosinolate concentrate is provided in a more or less pure form, with purity ranging typically from about 5% to about 100%, preferably 5%-80% and most preferably 5%-50%. In certain embodiments, the glucosinolate concentrate is obtainable by or obtained by isolation thereof from natural sources comprising glucosinolates, including plants or plant materials comprising glucosinolates. Plants comprising glucosinolates that may be used in accordance herewith include plants belonging to the plant families of Brassicaceae (Cruciferae), Akianaceae, Bataceae, Bretschneideraceae, Capparaceae, Caricaceae, Drypetes (Euphorbiaceae), Gyrostemonaceae, Limnanthaceae, Moringaceae, Pentadiplantdraceae, Resedaceae, Salvadoraceae, Tovariaceae and Tropeaolaceae. The plants in accordance herewith may readily be obtained by growing or culturing such plants using conventional agricultural practices. In preferred embodiments, the glucosinolate concentrate is obtainable from or obtained from a mustard plant. The term "mustard" and "mustard family" as used herein denotes any plant belonging to the family of Brassicaceae, including any plant belonging to the genera *Brassica, Sinapis* and *Erysimum*. Mustard plants that may be used in accordance with the present disclosure include, but are not limited to, *Brassica napus* (rapeseed), *Brassica juncea* (Oriental, Indian or brown mustard), *Brassica carinata* (Abyssinian or Ethiopian mustard), *Brassica nigra* (black mustard), *Brassica rapa* (rapeseed), *Sinapis alba* (yellow or white mustard), *Sinapis arvensis* (wild mustard), *Erysimum corinthium* and any cultivars or variant of the foregoing including the Canola cultivar of *Brassica napus*. In accordance herewith mixtures of any of the hereinbefore mentioned plants or plant materials may also be used.

The glucosinolate concentrate may be prepared by comminuting, plants, plant parts, plant portions or plant material or mixtures thereof, optionally washed. Plant material includes, but is not limited to, plant seeds, stems, roots or leaves obtainable from or obtained from plants of one of the hereinbefore mentioned plant species. Comminution may be achieved using a comminution means, for example a grinder or blender or another device capable of substantially fragmenting plant cell walls in the plant material. Furthermore a seed meal, preferably a de-oiled deed meal, may be obtained and used as a starting material from which the glucosinolate concentrate is prepared. Comminution of plant material is preferably performed in the presence of water or another aqueous extractant, including an aqueous buffer, or a lower alcohol or lower ketone or mixtures thereof. Glucosinolates, including sinigrin, will readily dissolve in such aqueous extractants. As used herein "lower alcohol" or "lower ketone" are $C_1$-$C_4$ alcohols and $C_3$-$C_4$ ketones. Furthermore it is particularly preferable that comminution is conducted at higher temperatures, i.e. a temperatures in excess of about 70° C., and more preferably in excess of about 80° C., and most preferably at about 95° C. Comminution at these temperatures will result in substantial irreversible inactivation of myrosinase, thus preventing the formation of glucosinolate breakdown products. Preferably a ratio of plant material to extractant, is less than or less than about 1:100 (w/v), more preferably less than or less than about 1:10 (w/v), and most preferably less than or less than about 1:1 (w/v). Comminution is preferably performed at temperatures between 4° C. or about 4° C. and 50° C. or about 50° C., and preferably between 18° C. or about 18° C., and 25° C. or about 25° C. In other embodiments, the comminution is performed in the absence of water, and water or another aqueous extractant, including an aqueous buffer, or a lower alcohol or lower ketone or mixtures thereof are subsequently mixed with the comminuted plant material. The solid comminuted plant material may be separated from the liquid fraction using a separation means, including but not limited to decantation, centrifugation, filtration or other means or method to separate the liquid fraction from the solids. Upon having obtained the liquid fraction, the extraction/separation step may be repeated one or more times, in order to achieve further removal of the solid. In addition the solid material may be extracted two or more times, in order to improve the yield. Centrifugation may additionally be used to separate plant oils, in embodiments where the communinuted plant material comprises plant oils, such as plant seed oils, from the aqueous fraction. The glucosinolates present in the liquid fraction may be concentrated and separated from other plant materials, using for example evaporation of the extractant and filtration, through for example one or more ion-exchange filtration steps, or through nano-filtration, to obtain a more purified concentrate. The glucosinolate concentrate may be freeze-dried, or spray dried in order to obtain a substantially dry glucosinolate concentrate. Concentrations of glucosinolate in the concentrate may vary from about 5% to about 100%, preferably 5%-80%, and most preferably 5%-50%. Additional methodologies providing glucosinolate concentrates from plants are described in PCT Patent Application WO2010023162; Toribio et al., 2007, J. of Chromatography, v 1170, (1-2), pp 44-51; and West et al., 2002, J of Chromatography v 996 (1-2), pp 227-232, which are incorporated herein, in their entirety, by reference. The glucosinolate concentrate prepared in accordance herewith is substantially free from glucosinolate breakdown products, and, in one aspect, is an inactive pesticide precursor.

Active Myrosinase Complex

In accordance with certain aspects hereof, the liquid compositions provided by the present disclosure comprise an active myrosinase complex in a concentration sufficient to release an effective amount of glucosinolate breakdown products upon the addition of water thereto. In preferred embodiments, the active myrosinase complex is obtained or obtainable from a plant material. Accordingly, in preferred embodiments, the liquid compositions provided by the present disclosure comprise a plant material comprising an active myrosinase complex in a concentration sufficient to release an effective amount of glucosinolate breakdown products upon the addition of water thereto. In certain embodiments, the plant material is a plant part or portion or processed plant material obtainable from a plant including, but not limited to the leaves, stems, roots or seeds of plants, or portions or mixtures thereof. Plants comprising myrosinases that may be used in accordance with the present disclosure include, but are not limited to, plants belonging to the plant families of Brassicaceae (Cruciferae), Akaniaceae, Bataceae, Bretschneideraceae, Capparaceae, Caricaceae, Drypetes (Euphorbiaceae), Gyrostemonaceae, Limnanthaceae, Moringaceae, Pentadiplantdraceae, Resedaceae, Salvodoraceae, Tovariaceae, and Tropaeolaceae, in all of which myrosinase complexes have been identified (Rodman, J. E. (1991) Phenetics. Systematic. Bot. 16: 598-618). In preferred embodiments, the plant material that is used is obtained or obtainable from a mustard plant. Mustard plants that may be used in accordance with the present disclosure include, but are not limited to, *Brassica napus* (rapeseed), *Brassica juncea* (Oriental, Indian or brown mustard), *Brassica carinata* (Abyssinian or Ethiopian mustard), *Brassica nigra* (black mustard), *Brassica rapa* (rapeseed), *Sinapis alba* (yellow or white mustard), *Sinapis arvensis* (wild mustard), *Erysimum corinthium* and any cultivars or varieties of the foregoing including the Canola cultivar of *Brassica napus*. Mixtures of plants or plant materials from the aforementioned plants may also be used.

In certain aspects of the present disclosure, the plant material as used herein is treated such as to produce a processed plant material comprising an active myrosinase complex or a plant extract comprising an active myrosinase complex. The plant material may be more or less processed in accordance herewith, and may be more or less wet or dry. Water concentrations may vary between about 2% and about 98%, and are preferably kept between about 1% and 6% or between 80% and 98%, depending on whether a relatively aqueous or relatively dry concentrate is desirable. In accordance with the present disclosure the plant material is prepared in such a manner that the myrosinase activity is retained. Preparation conditions suitable to retain myrosinase activity include temperatures are in general preferably kept below preferably 60° C. or about 60° C., more preferably below 45° C. or about 45° C. and most preferably below 30° C. or about 30° C. Under such conditions plant material comprising an active myrosinase complex may be obtained and used in accordance with the current disclosure. In certain embodiments of the present disclosure, plant material comprising substantive quantities of plant oils is used in accordance herewith, such as plant seeds. In such embodiments, it is preferable to separate the oil from the plant material. This may be accomplished through using for example, without limitation, solvent extraction means, hydraulic pressing means, expeller pressing means, cold pressing means and other oil removal means, which will be known to those of skill in the art, in order to obtain a de-oiled or defatted plant material. In other embodiments, other fractions or parts of the plant material may be removed. Thus seed husks may be removed from plant seed material to obtain a plant seed material comprising an active myrosinase complex. The active myrosinase complex may also be concentrated by processes such as extraction and fractionation of the extract. Extraction may be achieved using an aqueous extractant, including, but not limiting to, water, an aqueous buffer, or a lower alcohol or lower ketone or mixtures thereof. Further processing may optionally used to obtain plant material comprising myrosinase in a more concentrated form. Concentrations of active myrosinase complex in the plant material upon concentration may vary.

In certain aspects hereof, a dry plant material comprising an active myrosinase complex in a concentration sufficient to release an effective amount of glucosinolate breakdown products upon the addition of water is prepared. Such dry plant material may be prepared by the removal of endogenous water present in the plant material. Drying of the plant material in accordance herewith may achieved using a variety of methodologies such as, without limitation, processing of plant seed material through use of a grain drying means or a seed conditioning means designed to remove moisture from the material down to a defined level, which may be combined as hereinbefore mentioned with further processing of the plant material using aqueous extraction and fractionation. Other means that may be used in accordance herewith to obtain dried plant material comprising an active myrosinase complex include spray drying, flash drying and freeze drying means. The drying conditions applied are preferably relatively mild, however for very brief periods (milliseconds), where spray drying is used, temperatures may be relatively high, for example, about 150° C., or 120° C. or about 100° C. Flash drying temperatures are preferably between about 30° C. and about 80° C., and more preferably between about 40° C. and about 60° C. Freeze drying is conducted below 0° C. and more preferably below −18° C. Drying of the plant material may be performed before and/or after any other optional processing of the plant material. Upon completion of the drying of the plant material, the relative humidity of the plant material is preferably less than 10% or about 10%, and more preferably less than about 7% or 7%.

In accordance with certain aspects hereof, the present disclosure provides one embodiment in which the plant material comprising an active myrosinase complex in a concentration sufficient to release an effective amount of glucosinolate breakdown products upon the addition of water, is a seed meal. In such embodiment, the seed meal is preferably obtained from or obtainable from mustard seeds. In accordance with this embodiment, any process yielding a mustard seed meal comprising an active myrosinase complex in a concentration sufficient to release an effective amount of glucosinolate breakdown products upon the addition of water may be used. Mustard seed may readily obtained through conventional agricultural production of mustard plants. The mustard seed is preferably cleaned, in order to remove non-mustard plant material, and dried prior to further processing. In order to clean the mustard seed, the seed may be subjected to an elementary separation procedure, for example, but not limited to, by contacting the mustard seed with a separation means such as vibrating screen or a grain cleaning machine, for example, but not limited to, a grain cleaning machine such as manufactured by Damas A/S (Denmark). Through such operation the mustard seed may be separated from non-mustard seed material, such as rocks, sticks, dirt, leaves, weed seeds, loose hulls etc. Mustard seed may optionally be dried, using for example, but not limited to means used for grain drying, such as a grain dryer, for example a grain dryer as manufactured by Vertec Industries Limited (Canada). The grain drying means is operated so that the moisture content of the seed is reduced to between 5% or about 5% and 7% or about 7%. Dried mustard seed may be stored or mixed with other mustard seed. In order to prepare mustard seed meal, the outer seed coating, also known as the seed husk or bran, is optionally removed from the seed by milling or cracking the seed or using another suitable abrasive process to obtain the seed kernel. The oil or fat content in the seed meal that is prepared may vary. Full fat meals and defatted meals may both be used in accordance with the present disclosure. If a full fat meal is desired then the mustard seed, or optionally the seed kernels, are subjected to a process that does not result in oil extraction. If a defatted meal is desired then the seed, or optionally the seed kernels, are subjected to a process resulting in oil removal. In preferred embodiments of the present disclosure, a defatted meal is prepared. Accordingly the mustard seed or seed kernels are preferably ground using a grinding means, for example, without limitation, a hammer mill, to obtain mustard flour. The seed oil may be removed from the flour for example, without limitation, by organic solvent extraction, using for example, without limitation, hexane, or by mechanical separation from the non-oil components of the seed. Mechanical separation may be achieved using for example, without limitation, an oil expeller or press, such as an oil press such as a Taby Press manufactured by Skeppsta Maskin AB (Sweden) or a Komet oil expeller manufactured by Monforts Oekotec GmbH (Germany). A combination of mechanical oil removal followed by organic solvent extraction can also be used to achieve further removal of oil from the mustard seed. Preferably the mustard seed meal used in accordance with the present disclosure comprises between at least 2% or about 2% and no more than 50% or about 50% of the total seed oil content, and more preferably approximately between 10% or about 10%, and 15% or about 15%, and most preferably 15% or about 15% of the total seed oil content. The seed meal obtained comprises active myrosinase complex in a concentration sufficient to release an effective amount of glucosinolate breakdown products upon the addition of water. The amount of water present in the final myrosinase preparation may vary from 1-99%, e.g. between 60-90%, 70-90% or 80-90%. In preferred embodiments of the present disclosure, the mustard seed meal comprising active myrosinase complex has a moisture content of less than 12% or about 12%. Spray dried preparations may also be obtained and comprise from about 0.5% to 5%, or from about 1% to about 3% water. Many processes for processing raw mustard seed into oil and meal known to the art. Further processes that may be used are the processes disclosed in Morra, M. J, 2000-2002, Subcontract Report National Renewable Energy Laboratory NREL/SR-510-3628, which is incorporated herein in its entirety by reference.

Water Soluble Polyol

In accordance with certain aspects hereof, the liquid compositions provided by this disclosure comprise a water soluble polyol. The compositions according to the disclosure comprise at least one water-soluble polyol, preferably from the group of monomeric or polymeric non-cyclic polyols, and more preferably from the group of monomeric or polymeric non-cyclic polyols with 2 to 6 hydroxyl groups (e.g. 2, 3, 4, 5 or 6 hydroxyl groups), and having a molecular weight up to 20,000, wherein polymeric forms are obtainable from the addition of ethylene oxide and/or propylene oxide onto such polyols. All polyols are understood to be "water-soluble" when their solubility in water is at least 10 wt % at 20° C., thereby forming clear liquid solutions. "Non-cyclic polyols" are understood to be all polyols which in an aqueous solution do not substantially exist in equilibrium with a cyclic form.

In further preferred embodiments, the water soluble polyol is preferably from the group of non-cyclic polyols having 1 to 9 carbon atoms (e.g. 1, 2, 3, 4, 5, 6, 7, 8 or 9 carbon atoms) with 2 to 6 hydroxyl groups (e.g. 2, 3, 4, 5 or 6 hydroxyl groups). Preferred exemplary water-soluble polyols in this regard are 1,2-propylene glycol, 1,3 propylene glycol, diethylene glycol, 2-methyl-1,3-propane diol, glycerin, 1,2-butylene glycol, 1,3-butylene glycol, 1,4-butylene glycol, 1,2-pentane diol, 1,5-pentane diol, 1,2-hexane diol, 1,6-hexane diol, 1,2,6-hexane triol, 1,2-octane diol, 1,8-octane diol, dipropylene glycol, tripropylene glycerine, diglycerin, triglycerin, polyglycerin, as well as mixtures of the cited substances.

In particularly preferred embodiments, the water soluble polyol is glycerol. "Glycerol" or "glycerin", which may be used interchangeably herein, as defined in the present disclosure refers to a chemical compound having the structural formula (XV):

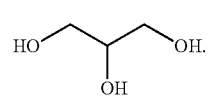

(XV)

In accordance herewith, glycerol is provided in liquid form, although it is noted that glycerol has a density of 1.26 g/cm$^3$ at 25° C. and is viscous at room temperature. In preferred embodiments, glycerol is provided in a more or less pure form. In accordance herewith glycerol is preferably provided at a purity level of at least 80% or about 80%, more preferably 97% or about 97%, or at least 99% or about 99%. Glycerol of the aforementioned purity grades may be readily obtained from a wide range of fine chemical manufacturers and/or distributors, including, for example, P&G Chemicals, and Cargill Inc.

In further particularly preferred embodiments, the water soluble polyol used herein is polyethylene glycol (PEG). As defined in the present disclosure "PEG" or "polyethylene glycol" refers to a chemical compound having the structural formula (XVI):

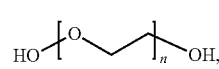

(XVI)

wherein n is an integer varying from 2-200, for example, n=3, 4, 5, 6, 7, 8, 9, 10, 12, 14, 16, 18, 20, 40, 60, 80 100, 150, or 200 (also known as PEG-3, PEG-4, PEG-5, PEG-6, PEG-7, PEG-8, PEG-9, PEG-10, PEG-12, PEG-14, PEG-16, PEG-18, PEG-20, PEG-40, PEG-60, PEG-80, PEG-100, PEG-150, and PEG-200, respectively) and has a molecular weight up to 20,000. In further embodiments, mixtures of any of the foregoing polyethylene glycols are also included herein. In preferred embodiments, polyethylene glycol is provided in a more or less pure form. In accordance herewith polyethylene glycol is preferably provided at a purity level of at least 80% or about 80%, more preferably 97% or about 97%, or at least 99% or about 99%. Polyethylene glycol of the aforementioned purity grades may be readily obtained from a wide range of fine chemical manufacturers and/or distributors, including, for example, P&G Chemicals, and Cargill Inc.

In further preferred embodiments, the water soluble polyol propylene glycol is used. "Propylene glycol" as used herein refers to 1,2 propylene glycol and/or 1,3 propylene glycol. 1,3 propylene glycol as used herein refers to a chemical compound having the structural formula (XVII):

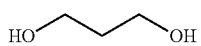

(XVII)

1,2 propylene glycol as used herein refers to a chemical compound having the structural formula (XVIII):

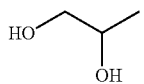

(XVIII)

In preferred embodiments, propylene glycol is provided in a more or less pure form. In accordance herewith, propylene glycol is preferably provided at a purity level of at least 80% or about 80%, more preferably 97% or about 97%, or at least 99% or about 99%. Propylene glycol of the aforementioned purity grades may be readily obtained from a wide range of fine chemical manufacturers and/or distributors, including, for example, P&G Chemicals, and Cargill Inc.

It has been found in accordance with the present disclosure, that in the presence of water soluble polyols, glucosinolates are not hydrolyzed, or not hydrolyzed to any substantive degree, thus permitting the preparation of a liquid formulation, notably a single liquid formulation, comprising a glucosinolate concentrate and a plant material comprising an active myrosinase complex. As used herein the term "not hydrolyzed to a substantive degree" means that when the glucosinolate concentrate and the plant material or extract thereof comprising active myrosinase complex are prepared in a liquid water soluble polyol formulation, the formulation is substantially free of glucosinolate breakdown products. As used herein the term "substantially free from glucosinolate breakdown products" means that the mixture is prepared in such a manner that the amount of glucosinolate breakdown products in the glucosinolate concentrate constitutes less than 10% (w/w), and more preferably less than or about 1.0% (w/w). Preferably the amount of glucosinolate breakdown products in the glucosinolate concentrate constitutes less than 0.5% (w/w) or about 0.5% (w/w), and most preferably no detectable amounts of glucosinolate breakdown products are present in the mixture. Thus the liquid pesticide formulations of the present disclosure are substantially free from any nitrile, including, but not limited to 1-cyano-2-hydroxy-3-butene and alyl cyanide; any thiocyanate, including, but not limited to, allyl thiocyanate, or isothiocyanate, including, but not limited to, allyl isothiocyanate; goitrin or epithionitrile obtained from hydrolysis of glucosinolate. Furthermore, it has been found in accordance herewith, that in the presence of water soluble polyols and water glucosinolates are not hydrolyzed to a substantive degree. In accordance with certain aspects hereof, the mixture is therefor substantially free from glucosinolate breakdown products. Thus the water soluble polyol used in accordance with the present disclosure may be mixed with a limited volume of water. With the term "a limited volume of water", it is meant a water volume which is sufficiently low to not result in the substantial hydrolysis of glucosinolates and the generation of glucosinolate breakdown products. Generally, as used herein such limited volumes vary from 1% (v/v) or about 1% (v/v) up to 80% (v/v) or about 80% (v/v). However, preferably, the water content is kept lower than 40% or about 40%, e.g. up to 1% (v/v) or about 1% water; up to 5% (v/v) or about 5% (v/v) water; up to 10% (v/v) or about 10% (v/v) water; up to 15% (v/v) or about 15% (v/v) water; up to 20% (v/v) or about 20% (v/v) water; up to 30% (v/v) or about 30% (v/v) water; up to 35% (v/v) or about 35% (v/v) water. Most preferably, the water content is kept from 0% up to 20% (v/v). Surprisingly, even in the presence of such quantities of water glucosinolate in the mixture is not hydrolyzed to a substantive degree. Water may be exogenously added water, or water may be used that is endogenously comprised in the glucosinolate concentrate prepared in accordance herewith or the plant material comprising myrosinase, and thus is mixed with the water soluble polyol in the preparation of the liquid formulations.

Preparation of Inactive Biopesticide Precursors

In accordance with certain aspects hereof, the present disclosure provides a liquid composition comprising an inactive biopesticide precursor substantially free of glucosinolate breakdown products, said liquid composition comprising: (a) a glucosinolate concentrate; (b) a plant material comprising an active myrosinase complex in a concentration sufficient to release an effective amount of glucosinolate breakdown products upon the addition of water; and (c) a water soluble polyol. In a preferred embodiment, the present disclosure provides a liquid composition comprising an inactive biopesticide precursor in a mixture substantially free of glucosinolate breakdown products, said mixture comprising: (a) a glucosinolate concentrate; (b) a plant material comprising an active myrosinase complex in a concentration sufficient to release an effective amount of glucosinolate breakdown products upon the addition of water; and (c) a water soluble polyol. In order to prepare the compositions of the present disclosure, the above ingredients are contacted with each other and mixed. Thus the present disclosure provides the glucosinolate concentrate and the plant material comprising the myrosinase in a single liquid formulation. In certain embodiments, the glucosinolate concentrate or the plant material, or both, are contacted with the water soluble polyol, or, optionally, the water soluble polyol water mixture, and they are mixed, prior to contacting the glucosinolate concentrate and the plant material comprising myrosinase with one another (this embodiment is further illustrated in Example 5). In other embodiments, the plant material and glucosinolate concentrate are mixed together and then contacted with the water soluble polyol (this embodiment is further illustrated in Example 4). In such embodiment, it is preferred that the plant material and glucosinolate concentrate are prepared as dry ingredients. In accordance herewith, the three component glucosinolate concentrate/myrosinase containing plant material/water soluble polyol mixture may be prepared and stored for use. In other embodiments, however a glucosinolate concentrate and plant material comprising myrosinase may be prepared as two separate components (with one or both ingredients comprising a water soluble polyol), and each component may be stored separately, with mixing to occur later, e.g. just prior to transportation to a site of intended use, or mixing may occur at a site of intended use as a pesticide, just prior to actual use. Conventional methodologies and means for mixing materials may be used, including for example any mechanical stirring or blending device. Mixing conditions may vary but mixing of the constituent compounds is typically performed at ambient temperatures and pressures and in such a manner that a homogenous mixture is obtained. Mixing times may vary, and it is noted that it may be beneficial upon initial mixing to let the mixture settle for a brief period (e.g. 15 mins; 30 mins; 60 mins) prior to the initiation of application to the pest. Water used in accordance herewith may comprise additional agents, e.g. water comprising buffering agents, salts, trace amounts of metals, and the like may be used. Thus, when referring herein to diluting the mixture of active ingredients with water, it is understood that the term "water" includes, tap water, irrigation water, deionized water, water comprising buffering agents, and so forth, and, as such, the term is understood to encompass water-based diluents. In accordance with the present disclosure, the myrosinase is present in the mixture in a concentration that is sufficient to release an effective amount of glucosinolate breakdown products upon the addition of water. "Effective amount" as used herein is any amount that results in the reduction of the severity or detrimental effect caused by a pest for a limited or prolonged period of time. In preferred embodiments, the plant material is provided such that the myrosinase present therein is present in the final liquid composition in a concentration of between 1 or about 1 units per gram and between 50 units, or about 50 units, per gram, however concentrations may be as low as 0.1 units, or about 0.1 units, per gram of the final liquid composition. The glucosinolate concentrate is provided typically such that it is present in the final liquid composition in concentrations varying between 25 mg/g or about 25 mg/g and 500 mg/g or about 500 mg/g. The water soluble polyol, or optionally the water soluble polyol water mixture, is provided in such a manner that it constitutes from about 60% (v/w) to about 95% (v/w), and, preferably, from about 70% (v/w) to about 95% (v/w) of the mixture. In a preferred embodiment, the enzyme activity to sinigrin ratio in the final liquid product would be 100-250 units of enzyme activity to 1 g of sinigrin. Using the aforementioned concentrations and amounts, the plant material and the glucosinolate concentrate readily dissolve or disperse in the water soluble polyol, while the final formulation remains in a liquid state.

The mixtures prepared in accordance with the present disclosure further may comprise additional constituent compounds. These constituent compounds include myrosinase enzyme catalysts including, but not limited to, ascorbic acid, magnesium chloride or other metal chloride, or a buffering agent, including but not limiting to a phosphate buffer.

As hereinbefore mentioned, the present disclosure, in a further embodiment, provides a method for making a liquid composition comprising an inactive biopesticide precursor comprising mixing:
  (a) a glucosinolate concentrate;
  (b) an active myrosinase complex in a concentration sufficient to release an effective amount of glucosinolate breakdown products upon the addition of water; and
  (c) a water soluble polyol.
  to obtain a mixture substantially free of glucosinolate breakdown products.

In preferred embodiments of the present disclosure, mustard seed meal is used as the source of active myrosinase complex.

Use of the Pesticide Formulations

The liquid compositions provided herein are pesticidally inactive, provided however, that the addition of water to the compositions, renders the compositions pesticidally active. The addition of water will result in glucosinolate hydrolysis and the generation of glucosinolate breakdown products thus providing a pesticidally active product. Accordingly, the present disclosure further provides a method for controlling pests comprising:
  (a) adding water to a liquid composition comprising an inactive biopesticide precursor substantially free of glucosinolate breakdown product, said liquid composition comprising:
    (i) a glucosinolate concentrate;
    (ii) an active myrosinase complex in a concentration sufficient to release an effective amount of glucosinolate breakdown products upon the addition of water to the liquid composition;
    (iii) a water soluble polyol; and
  (b) applying the liquid composition to a pest.

Accordingly, the present disclosure still further provides a method for controlling pests comprising:
  (a) providing a liquid composition comprising an inactive biopesticide precursor substantially free of glucosinolate breakdown product, said liquid composition comprising:
    (i) a glucosinolate concentrate;
    (ii) an active myrosinase complex in a concentration sufficient to release an effective amount of glucosinolate breakdown products upon the addition of water to the liquid composition; and
    (iii) a water soluble polyol;
  (b) adding water to the liquid composition to obtain a diluted liquid composition; and
  (c) applying the diluted liquid composition to a pest.

In accordance with the present disclosure, after the liquid composition of glucosinolate concentrate, plant material comprising an active myrosinase complex, and water soluble polyol has been provided and/or prepared, a sufficient volume of water is added to obtain a diluted liquid composition. Surprisingly, in accordance with the present disclosure, it has been found that upon mixing with a sufficient quantity of water and obtaining a diluted liquid composition, the hydrolytic activity of the myrosinase enzyme may be substantially reconstituted, thus the impact of the water soluble polyol on the myrosinase is negligibly small. The term "sufficient volume of water" as used herein refers to an amount of water that results in the substantial hydrolysis of glucosinolate, and generation of glucosinolate breakdown products. The amount of water added may vary, but comprises preferably a volume at least equal to the volume of the liquid composition, or at least 2 times the volume of the liquid composition, and is more typically added in a quantity of at least 3 or about 3 times, at least 5 times, or at least 10 times or more of the volume of the liquid composition.

As noted, upon the addition of a sufficient quantity of water to the liquid composition, the myrosinase activity may be substantially reconstituted in the diluted liquid composition, with the preparation exhibiting substantial enzymatic activity. "Substantial enzymatic activity" as used herein refers to a preparation that may be used as a pesticidally active product, i.e. a product that is capable of reducing the incidence or severity of a pest. In preferred embodiments, a preparation exhibiting substantial enzymatic activity exhibits, upon mixing with sufficient quantities of water, a rate of glucosinolate hydrolysis of at least 10% or about 10% of the rate relative to a liquid formulation prepared without a water soluble polyol, more preferably, at least 20%, 30%, 40%, 50%, 60%, 70%, 80%, 90%, 95% or 99%. Thus, by way of example, if a liquid formulation without a water soluble polyol is prepared to comprise 6 units/gram of myrosinase activity, such liquid formulation prepared in accordance with the methodology of the present disclosure, upon mixing with a sufficient quantity of water to obtain a diluted liquid composition, comprises at least preferably 0.6 units/gram, or about 0.6 units/gram, of myrosinase activity. As will be clear from the foregoing, the enzymatic activity of the diluted liquid composition may vary, provided however, that in accordance with the disclosure, the enzymatic activity is sufficient to provide a pesticidally active product.

It is a particularly advantageous feature of the present disclosure that the liquid compositions of the disclosure are readily miscible with water. In this regard it is noted that carriers commonly used in pesticide formulations, in particular oil based carriers, do not readily dissolve in water.

In further embodiments, the present disclosure provides a pesticide application kit containing a liquid formulation comprising:
  (c) a glucosinolate concentrate;
  (d) an active myrosinase complex in a concentration sufficient to release an effective amount of glucosinolate breakdown products upon the addition of water; and
  (c) a water soluble polyol,
  together with instructions regarding the addition of water to the liquid formulation to form a diluted liquid formulation and subsequent application to a pest. The instructions may be included with the kit (e.g. printed on paper and provided directly with the kit), or a reference may be provided for on-line access to the instructions, all of which are intended to be included herein. The instructions may additionally comprise further information regarding the products and its use, e.g. safety information.

In further embodiments, the present disclosure provides a pesticide application kit containing a liquid formulation comprising:
  (a) a glucosinolate concentrate; and
  (b) an active myrosinase complex in a concentration sufficient to release an effective amount of glucosinolate breakdown products upon the addition of water,
  wherein either or both of the glucosinolate concentrate or the active myrosinase complex are dissolved in a water soluble polyol, and together with instructions regarding the, mixing of the glucosinolate concentrate and the myrosinase complex and the addition of water to the liquid formulation to form a diluted liquid formulation and subsequent application to a pest. The instructions may be included with the kit (e.g. printed on paper and included with the kit), or a reference may be provided for on-line access to the instructions. The instructions may additionally comprise further information regarding the products and its use, e.g. safety information.

One further particularly advantageous feature of the present disclosure is that a biopesticide precursor is provided which may be stored and transported in an inactive form. Accordingly, in preferred embodiments, activation is controlled by adding water to the mixture at the site of pesticide use. In a particularly preferred embodiment, in accordance with the present disclosure the liquid composition is introduced into an agricultural irrigation system, through for example an input port in an irrigation pipe or hose of the system. Thus in this embodiment water is added to the mixture by contacting the mixture with irrigation water of an agricultural irrigation system. The liquid composition then is applied to the pest, for example by dripping or sprinkling, and operation of the irrigation system.

The target pest may be any pest, including any prokaryotic pest, including any prokaryotic pest belonging to the Monera kingdom, and any eukaryotic pest belonging to the Protista, fungal, plant and animal kingdoms, including further any pest capable of damaging an agricultural crop. Accordingly pests to which the compositions of the present disclosure may be applied include any insect, arachnid or crustacean pest, including ticks, mites, weevils, ants, lygus bugs mosquitoes etc. Fungal pests that may be treated with the compositions of the present disclosure include, but are not limited to, *Verticillium, Fusarium, Phytium, Sclerotina* and fungal species belonging to the order of Erisphales (powdery mildew). Further pests to which the compositions of the present disclosure may be applied are worms, nematodes, snails, slugs and white grubs. The final applied liquid composition may be a spray, or a fluid and or any other liquid form as desired, and may be applied using any spraying device or irrigation system or any other suitable system capable of application of a liquid pesticide. The delivery route to the pests may vary and may be as desired for example the pesticide product may be delivered through aquatic exposure or direct contact. Upon application of the pesticide to the pest, the incidence or severity of the pest infestation or activity will be limited or reduced at least for a limited or more prolonged period of time, and as such the novel methods and compositions disclosed herein provide a means to control pests.

EXAMPLES

Hereinafter are provided examples of specific embodiments for performing the methods of the present disclosure, as well as embodiments representing the compositions of the present disclosure. The examples are provided for illustrative purposes only, and are not intended to limit the scope of the present disclosure in any way.

Example 1

Preparation of a Liquid Biopesticide Formulation Comprising Propylene Glycol Three dry myrosinase/sinigrin samples were prepared, each sample containing: 0.025 g milled *Sinapis alba* meal (containing active myrosinase), and 0.075 g of a particulate sinigrin concentrate (containing approximately 25% pure sinigrin). Two propylene glycol solutions were prepared as follows: a first solution containing (80% (v/v) propylene glycol (1,3 propane diol)/20% (v/v) water), ascorbic acid (1 mM), $MgCl_2$ (1 mM) and potassium phosphate buffer (pH 6.5); and a second solution containing 60% (v/v) propylene glycol 1,3 propane diol/40% (v/v) water), ascorbic acid (1 mM), $MgCl_2$ (1 mM) and potassium phosphate buffer (pH 6.5). A control was prepared containing 100% (v/v) water as the water, ascorbic acid, $MgCl_2$ and potassium phosphate buffer (pH 6.5). The three myrosinase/sinigrin samples were mixed with 4 ml of the first and second propylene glycol solutions in a sealable glass vial (i.e. the (80% (v/v) propyelene glycol (1,3 propane diol)/20% (v/v) solution; labeled "80/20" in Table 1 below; and the 60% (v/v) propylene glycol (1,3 propane diol)/40% (v/v) solution; labeled "60/40" in Table 1 below) and with the control (labeled "$H_2O$" in Table 1 below). Upon sealing the glass vial it was incubated at room temperature and intermittently shaken. The headspace above the liquid formulation was tested for the presence of AITC at certain time intervals (1 hr; 23 hrs) using a Head Space Gas Chromatography (HSGC) system and the AITC peak area was determined. The results are shown in Table 1 below.

TABLE I

| Sample | AITC (Peak Area) | |
|---|---|---|
| | t = 1 hr | t = 23 hrs |
| 80/20 | 1 | 10 |
| 60/40 | 57 | 75 |
| H$_2$0 | 377 | 347 |

Example 2

Preparation of a Liquid Biopesticide Formulation Comprising Glycerol

Three dry myrosinase/sinigrin samples were prepared, each sample containing: 0.025 g milled *Sinapis alba* meal (containing active myrosinase), and 0.075 g of a particulate sinigrin concentrate (containing approximately 25% pure sinigrin). Two polyethylene glycol solutions were prepared as follows: a first solution containing (80% (v/v) glycerol/20% (v/v) water), ascorbic acid (1 mM), MgCl$_2$ (1 mM) and potassium phosphate buffer (pH 6.5); and a second solution containing 60% (v/v) glycerol/40% (v/v) water), ascorbic acid (1 mM), MgCl$_2$ (1 mM) and potassium phosphate buffer (pH 6.5). A control was prepared containing 100% (v/v) water as the water, ascorbic acid, MgCl$_2$ and potassium phosphate buffer (pH 6.5). The three myrosinase/sinigrin samples were mixed with 4 ml of the first and second glycerol solutions in a sealable glass vial (i.e. the (80% (v/v) glycerol/20% (v/v) solution; labeled "80/20" in Table 11 below; and the 60% (v/v) glycerol/40% (v/v) solution; labeled "60/40" in Table II below) and with the control (labeled "H$_2$O" in Table II below). Upon sealing the glass vial it was incubated at room temperature and intermittently shaken. The headspace above the liquid formulation was tested for the presence of AITC at certain time intervals (1 hr; 23 hrs) using a Head Space Gas Chromatography (HSGC) system and the AITC peak area was determined.

TABLE II

| Sample | AITC (Peak Area) | |
|---|---|---|
| | t = 1 hr | t = 23 hrs |
| 80/20 | 28 | 99 |
| 60/40 | 156 | 277 |
| H$_2$0 | 377 | 347 |

Example 3

Preparation of a Liquid Biopesticide Formulation Comprising Polyethylene Glycol

Three dry myrosinase/sinigrin samples were prepared, each sample containing: 0.025 g milled *Sinapis alba* meal (containing active myrosinase), and 0.075 g of a particulate sinigrin concentrate (containing approximately 25% pure sinigrin). Two polyethylene glycol solutions were prepared as follows: a first solution containing (80% (v/v) polyethylene glycol (PEG200)/20% (v/v) water), ascorbic acid (1 mM), MgCl$_2$ (1 mM) and potassium phosphate buffer (pH 6.5); and a second solution containing 60% (v/v) polyethyelene glycol (PEG200)/40% (v/v) water), ascorbic acid, MgCl$_2$ and potassium phosphate buffer (pH 6.5). A control was prepared containing 100% (v/v) water as the water, ascorbic acid (1 mM), MgCl$_2$ (1 mM) and potassium phosphate buffer (pH 6.5). The three myrosinase/sinigrin samples were mixed with 4 ml of the first and second polyethylene glycol (PEG200) solutions in a sealable glass vial (i.e. the (80% (v/v) polyethylene glycol (PEG200)/20% (v/v) solution; labeled "80/20" in Table III below; and the 60% (v/v) polyethylene glycol (PEG200)/40% (v/v) solution; labeled "60/40" in Table III below) and with the control (labeled "H$_2$O" in Table III below). Upon sealing the glass vial it was incubated at room temperature and intermittently shaken. The headspace above the liquid formulation was tested for the presence of AITC at certain time intervals (1 hr; 23 hrs) using a Head Space Gas Chromatography (HSGC) system and the AITC peak area was determined.

TABLE III

| Sample | AITC (Peak Area) | |
|---|---|---|
| | t = 1 hr | t = 23 hrs |
| 80/20 | not detected | not detected |
| 60/40 | 11 | 27 |
| H$_2$0 | 377 | 347 |

Example 4

Reconstitution of Enzyme Activity (Mixed System)

Myrosinase/sinigrin samples were prepared as in Examples 1 and 3 comprising propylene glycol (1,3 propanediol) and polyethylene glycol (PEG-200), except that for both water soluble polyols a 90% (v/v) polyol/10% water and a 80% (v/v)/20% (v/v) water was prepared, and except that the preparation was not buffered and no ascorbic acid and MgCl$_2$ was included in the preparation. The liquid samples were mixed in a glass vial, sealed and stored for 46 hrs. After 46 hrs the liquid samples were diluted using 3 mls of water/potassium phosphate buffer (pH 6.5)/MgCl$_2$ (0.1 mM)/ascorbic acid (0.1 mM) and the samples were assayed at different time points (t=0 mins; t=30 mins; t=65 mins and t=125 mins). A freshly prepared myrosinase/sinigrin sample in water was used as a control and it was assayed at t=15 mins and t=30 mins. Assays were conducted using a Head Space Gas Chromatography (HSGC) system and the AITC peak area was determined.

The results are shown in Table IV (propylene glycol) and Table V (polyethylene glycol) below.

TABLE IV

| Sample | AITC (Peak Area) | | | |
|---|---|---|---|---|
| | t = 0 mins | t = 30 mins | t = 65 mins | t = 125 mins |
| 80/20 PG | 21.2 | 68.7 | 106.8 | 155.5 |
| 90/10 PG | 1.4 | 53.8 | 122.9 | 203.9 |

TABLE IV-continued

| | AITC (Peak Area) | |
|---|---|---|
| Control | t = 15 min | t = 30 min |
| $H_2O$ | 358.2 | 347.6 |

TABLE V

| | AITC (Peak Area) | | | |
|---|---|---|---|---|
| Sample | t = 0 mins | t = 30 mins | t = 65 mins | t = 125 mins |
| 80/20 PEG | 5.8 | 53.6 | 96.9 | 140.1 |
| 90/10 PEG | not detected | 33.5 | 73.3 | 121.9 |

| | AITC (Peak Area) | |
|---|---|---|
| Control | t = 15 min | t = 30 min |
| $H_2O$ | 358.2 | 347.6 |

Example 5

Reconstitution of Enzyme Activity (2 Component System)

Two separate myrosinase and two separate sinigrin solutions were prepared, each solution containing glycerol or propylene glycol (1,3 propanediol) (for both water soluble polyols 80% (v/v)/20% (v/v) water). The final preparations contained 0.15 g/g sinigrin extract and 0.05 g/g *Sinapis alba* meal, respectively. The liquid samples were sealed and stored separately stored for 48 hrs. After 48 hrs, an aliquot of 0.5 g of each of the myrosinase and sinigrin samples was drawn, and both were added together and incubated for 30 mins, and both the propylene glycol stored material and the glycerol stored material was assayed for enzyme activity (t=30 mins). Thereafter 3 mls of water/potassium phosphate buffer (pH 6.5)/$MgCl_2$ (0.1 mM)/ascorbic acid (0.1 mM) was added and the enzyme activity using both the propylene glycol stored material and the glycerol stored material was assayed at additional time points (t=60 mins and t=120 mins). A freshly prepared myrosinase/sinigrin sample in water was used as a control and its enzyme activity was measured at various time points (t=15 mins and t=30 mins). All assays were performed using a Head Space Gas Chromatography (HSGC) system and the AITC peak area was determined. The results are shown in Table VI.

TABLE VI

| | AITC (Peak Area) | | |
|---|---|---|---|
| Sample | t = 30 mins | t = 60 mins | t = 120 mins |
| Glycerol | 30.2 | 351.9 | 326.2 |
| Propylene Glycol | not detected | 249.7 | 267.8 |

| | AITC (Peak Area) | |
|---|---|---|
| Control | t = 15 min | t = 30 min |
| $H_2O$ | 358.2 | 347.6 |

TABLE VII

| Additional Exemplary Glucosinolates | |
|---|---|
| Trivial Name | Structure of R-Group |
| Gluconapolieferin | 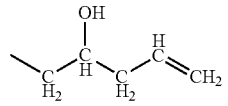 |
| Gluconapin | 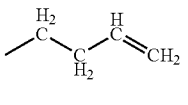 |
| Glucobrassicanapin | 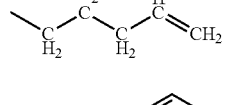 |
| Gluconasturtlin | 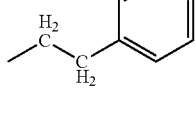 |
| Glucobrassicin | 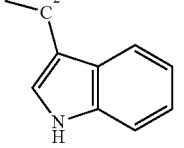 |
| 4-hydroxy-glucobrassicin |  |
| 4-methoxy-glucobrassicin | 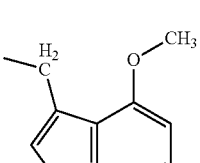 |
| neoglucobrassicin | 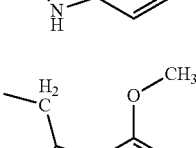 |
| Glucoraphenin | 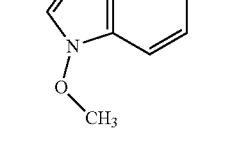 |
| Glucoraphanin | 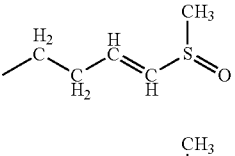 |

TABLE VII-continued

Additional Exemplary Glucosinolates

| Trivial Name | Structure of R-Group |
|---|---|
| Glucocochlearin | (isobutyl group) |
| Glucoiberin | CH₃-S(=O)-CH₂-CH₂- |
| Glucoiberverin | CH₃-S-CH₂-CH₂- |
| Glucocheirolin | CH₃-S(=O)₂-CH₂-CH₂- |
| Glucoapparin | -CH₃ |
| Glucoalyssin | CH₃-S(=O)-CH₂-CH₂-CH₂-CH₂- |
| Glucoaubrietin | 4-methoxybenzyl |
| Glucobarbarin | C₆H₅-CH(OH)-CH₂- |
| Glucolepidin | ethyl |
| Glucolimnantin | 3-methoxybenzyl |
| Glucoiesquerelin | CH₃-S-CH₂-CH₂-CH₂-CH₂-CH₂- |
| Glucojirsutin | CH₃-S-CH₂-CH₂-CH₂-CH₂-CH₂-CH₂- |
| Glucoarabin | CH₃-S-CH₂-CH₂-CH₂-CH₂-CH₂-CH₂-CH₂- |
| Glucoerucin | CH₃-S-CH₂-CH₂-CH₂-CH₂- |

The invention claimed is:

1. A liquid composition comprising an inactive biopesticide precursor substantially free of glucosinolate breakdown products, said liquid composition comprising:
   (a) a glucosinolate concentrate;
   (b) an active myrosinase complex in a concentration sufficient to release an effective amount of glucosinolate breakdown products upon the addition of water; and
   (c) a water soluble polyol.

2. The composition according to claim 1 wherein the active myrosinase complex is obtainable from a plant material.

3. The composition according to claim 2 wherein the plant material is obtainable from a mustard plant.

4. The composition according to claim 2 wherein the plant material is a seed meal.

5. The composition according to claim 2 wherein the plant material is a mustard seed meal.

6. The composition according to claim 2 wherein the water soluble polyol is at least about 80% pure.

7. The composition according to claim 2 wherein the composition additionally comprises at least about 1% water and up to about 20% water.

8. The composition according to claim 2 wherein the active myrosinase complex is present in a concentration of from about 1 unit to about 10 units per gram in the composition and the glucosinolate is present from about 25 mg to about 500 mg per gram in the composition.

9. The composition according to claim 8 wherein upon the addition of water to the composition, the myrosinase complex is substantially enzymatically active.

10. The composition according to claim 1 further comprising a compound selected from the group of compounds consisting of magnesium chloride and ascorbic acid.

11. The composition according to claim 1 wherein the water soluble polyol is selected from the group consisting of glycerol, polyethylene glycol and propylene glycol.

* * * * *